United States Patent
Steel et al.

(10) Patent No.: US 9,889,249 B2
(45) Date of Patent: Feb. 13, 2018

(54) NEEDLE ASSEMBLY MAGAZINE

(71) Applicant: SANOFI-AVENTIS DEUTSCHLAND GMBH, Frankfurt am Main (DE)

(72) Inventors: Samuel Steel, Warwickshire (GB); Paul Richard Draper, Worcestershire (GB); Joseph Butler, Warwickshire (GB); George Cave, Warwickshire (GB); David Richard Mercer, Warwickshire (GB); Sophie Louise Sladen, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 194 days.

(21) Appl. No.: 14/650,158

(22) PCT Filed: Nov. 29, 2013

(86) PCT No.: PCT/EP2013/075135
§ 371 (c)(1),
(2) Date: Jun. 5, 2015

(87) PCT Pub. No.: WO2014/086684
PCT Pub. Date: Jun. 12, 2014

(65) Prior Publication Data
US 2016/0000992 A1    Jan. 7, 2016

(30) Foreign Application Priority Data

Dec. 7, 2012    (EP) ..................................... 12196101

(51) Int. Cl.
*A61M 5/00*    (2006.01)
*A61M 5/32*    (2006.01)
(Continued)

(52) U.S. Cl.
CPC ......... *A61M 5/002* (2013.01); *A61B 50/3001* (2016.02); *A61M 5/3205* (2013.01); *B65D 85/24* (2013.01); *A61M 2005/004* (2013.01)

(58) Field of Classification Search
CPC ................ A61M 5/002; A61M 5/3205; A61M 2005/004; B65D 85/24; A61B 50/3001
See application file for complete search history.

(56) References Cited

U.S. PATENT DOCUMENTS

2002/0020646 A1*  2/2002  Groth .................... A61M 5/002
                                                        206/366
2004/0260270 A1* 12/2004  Cohen .................... A61M 5/20
                                                        604/506
(Continued)

FOREIGN PATENT DOCUMENTS

WO    WO 2001/093927    12/2001
WO    WO 2004/110299    12/2004

OTHER PUBLICATIONS

Extended European Search Report in Application No. 12196101.5, dated Apr. 5, 2013, 7 pages.
(Continued)

*Primary Examiner* — Bhisma Mehta
*Assistant Examiner* — Hamza Darb
(74) *Attorney, Agent, or Firm* — Fish & Richardson P.C.

(57) ABSTRACT

Described is a needle assembly magazine comprising a housing including a coupling having a proximal aperture adapted to receive a medicament delivery device and a distal aperture adapted to receive a needle of a needle assembly, a needle guard coupled to the housing and having an aperture axially aligned with the distal aperture of the coupling, and a needle assembly carrier rotatably coupled to the needle guard and adapted to hold a plurality of needle assemblies.

(Continued)

Rotation of the needle assembly carrier aligns one needle assembly with the distal aperture and the aperture.

17 Claims, 18 Drawing Sheets

(51) Int. Cl.
    *B65D 85/24*         (2006.01)
    *A61B 50/30*        (2016.01)

(56)               References Cited

U.S. PATENT DOCUMENTS

2008/0312604 A1* 12/2008 Boesen ................. A61M 5/008
                                                                   604/207
2012/0041381 A1* 2/2012 Raj ....................... A61M 5/002
                                                                   604/192
2015/0025469 A1* 1/2015 Larsen .................. A61M 5/002
                                                                   604/173

OTHER PUBLICATIONS

International Preliminary Report on Patentability in International Application No. PCT/EP2013/075135, dated Jun. 9, 2015, 8 pages.
International Search Report and Written Opinion in International Application No. PCT/EP2013/075135, dated Feb. 5, 2014, 11 pages.

\* cited by examiner

NEEDLE ASSEMBLY MAGAZINE

This application is a 371 U.S. National Application of PCT/EP2013/075135, filed on Nov. 29, 2013, which claims priority to European Patent Application No. 12196101.5, filed on Dec. 7, 2012, the entire contents of which are incorporated herein by reference.

TECHNICAL FIELD

The invention relates to a needle assembly magazine.

BACKGROUND OF THE INVENTION

Conventional medicament delivery devices typically require a needle assembly for creating a fluid path between a medicament container and a needle. It is generally recommended to use an unused injection needle for each injection in order to reduce the risk for cross contamination, infection and pain associated with reuse of used needles.

Many users of medicament delivery devices, such as pen injectors and autoinjectors, may be elderly or have reduced dexterity. For these groups, mounting needle assemblies to the delivery device may be problematic if the needle assembly is not oriented corrected, which may disrupt the fluid path for the medicament or may lead to a painful injection process. Further, removing used injection needles can be difficult and may subject the user to the risk of needle stick injuries. Generally, it is recommended that needles be removed with care to avoid needle stick injury.

Further, users of medicament delivery devices are required to carry multiple needle assemblies, for example, when travelling. Currently, unused needle assemblies are contained in large boxes, which are not especially portable.

Thus, there remains a need for an improved needle assembly magazine which facilitates needle assembly mounting and removal on/from a medicament delivery device and enhances portability of multiple needle assemblies.

SUMMARY OF THE INVENTION

It is an object of the present invention to provide an improved needle assembly magazine.

In an exemplary embodiment, a needle assembly magazine according to the present invention comprises a housing including a coupling having a proximal aperture adapted to receive a medicament delivery device and a distal aperture adapted to receive a needle of a needle assembly, a needle guard coupled to the housing and having an aperture axially aligned with the distal aperture of the coupling, and a needle assembly carrier rotatably coupled to the needle guard and adapted to hold a plurality of needle assemblies. Rotation of the needle assembly carrier aligns one needle assembly with the distal aperture and the aperture.

In an exemplary embodiment, the coupling includes a thread, a bayonet arrangement, a friction fit arrangement or a snap fit arrangement adapted to engage a distal end of the medicament delivery device.

In an exemplary embodiment, the needle guard is translatable relative to the housing from an extended position to a retracted position.

In an exemplary embodiment, the needle assembly magazine further comprises a guard spring biasing the needle guard in the extended position.

In an exemplary embodiment, the needle has a proximal tip and a distal tip, and the needle assembly further comprises a needle hub adapted to hold the needle. The needle hub is slidably disposed in an aperture in the needle assembly carrier and can move between from a retracted position to an extended position relative to the needle assembly carrier. The needle assembly further comprises a needle spring biasing the needle assembly in the retracted position.

In an exemplary embodiment, the needle assembly carrier includes ratchets adapted to engage a resilient arm on the needle guard. The resilient arm deflects due to engagement by a ratchet when the needle assembly carrier rotates in a first rotational direction and abuts a ratchet preventing rotation of the needle assembly carrier in a second rotational direction.

In an exemplary embodiment, the needle assembly carrier includes a plurality of grip features, wherein at least one of the grip features extends through a cut-out in the needle guard.

In an exemplary embodiment, movement of the needle guard from the extended position to the retracted position causes the needle hub to abut the housing and move from the retracted position to the extended position to (i) project the proximal tip of the needle through the distal aperture of the coupling and (ii) project the distal tip of the needle through the distal aperture of the needle guard.

In an exemplary embodiment, at least one indicia is disposed on the needle assembly carrier, and at least one of the at least one indicia is viewable through a cut-out in the needle guard. The at least one indicia includes a number, a graphic, an image, a word, or a color.

In an exemplary embodiment, the needle assembly carrier comprises a proximal plate and a distal plate. Each of the plates includes apertures for holding the needle assemblies. A carrier spring biases the proximal plate relative to the distal plate. The proximal plate includes a stem having a track adapted to engage a drive tooth on the housing. The track includes a first longitudinal channel and a second longitudinal channel coupled by an angled portion.

In an exemplary embodiment, a button may be coupled to the housing and adapted to engage the proximal plate. Axial movement of the button relative to the housing from an extended position to a retracted position causes the drive tooth to travel axially in the first longitudinal section, and movement of the button relative to the housing from the retracted position to the extended position causes the drive tooth to travel along the angled position and into the second longitudinal channel, thereby rotating the proximal plate relative to the needle guard. A button spring may bias the button in the extended position.

The exemplary embodiments of the needle assembly magazine according to the present invention make it quicker and easier to change needle assemblies on a medicament delivery device, reduce the risk of needle stick injuries and reduce the space required to store needles assemblies.

The needle assemblies never have to be touched, which substantially reduces the risk of injury. After all of the needle assemblies in the needle assembly magazine are used, the needle assembly magazine can be discarded and replaced with a new magazine.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
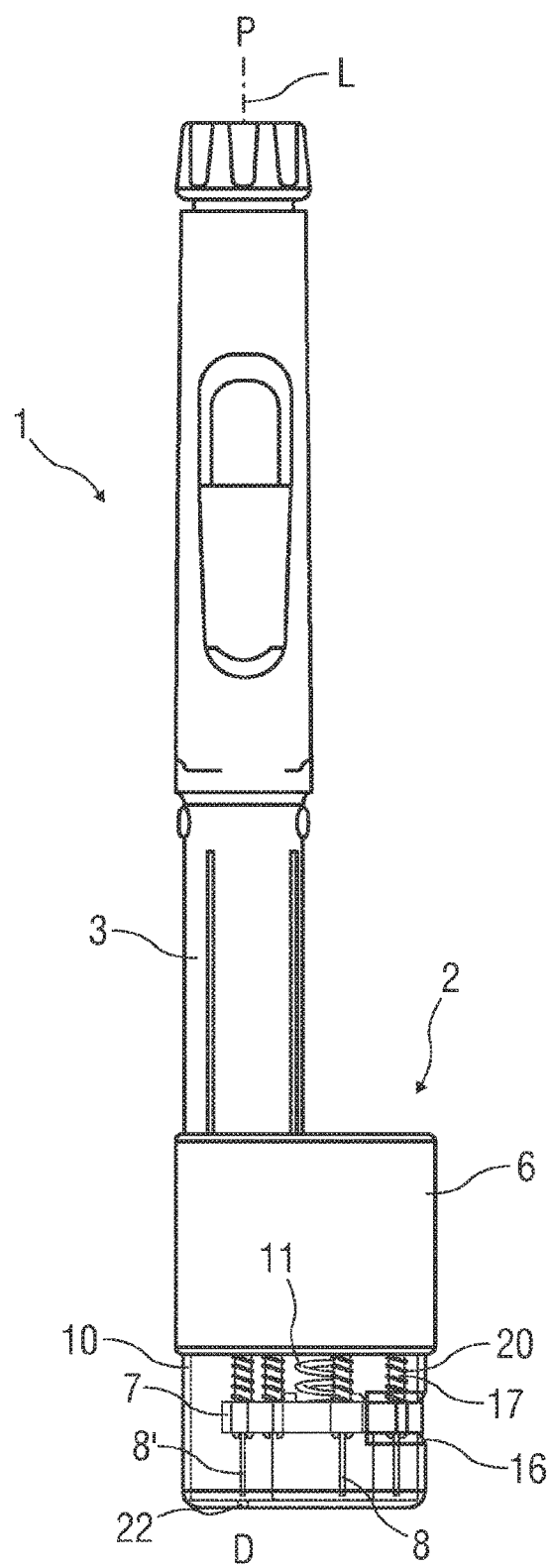
FIG. 1 is a schematic side view of an exemplary embodiment of a medicament delivery device with a needle assembly magazine.

FIG. 1 is a schematic side view of an exemplary embodiment of a medicament delivery device 1 with a needle assembly magazine 2. The medicament delivery device 1 may be, for example, a pen injector, an autoinjector, a prefilled syringe, etc. In the exemplary embodiment shown in FIG. 1, the medicament delivery device 1 includes a cartridge holder portion 3 adapted to hold a cartridge (e.g., syringe, ampoule, etc.) containing a medicament. A needle assembly magazine 2 is adapted to engage a distal end of the medicament delivery device 1.

Figure 2:
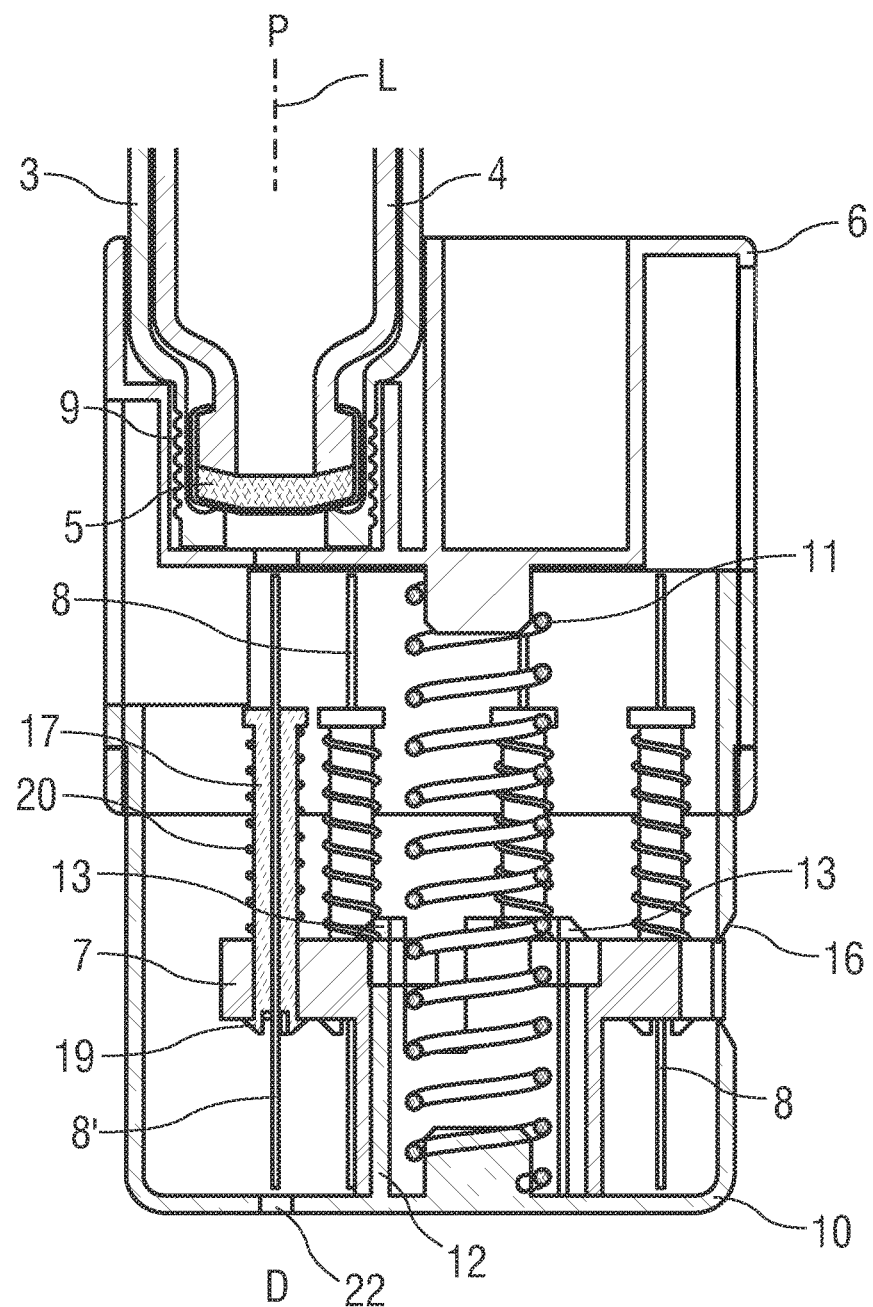
FIG. 2 is a schematic detail longitudinal section of an exemplary embodiment of a needle assembly magazine.

FIG. 2 is a schematic detail longitudinal section of an exemplary embodiment of the needle assembly magazine 2. A cartridge 4 is disposed in the medicament delivery device 1, and the cartridge 4 is sealed by a septum 5. The needle assembly magazine 2 comprises a housing 6 having a coupling 9 which is adapted to engage the distal end of the medicament delivery device 1. The coupling 9 may be, for example, threads adapted to engage corresponding threads on the medicament delivery device 1. In other exemplary embodiments, the coupling 9 may be a bayonet coupling, a friction fit, a snap fit, etc. The coupling 9 may include an aperture which facilitates alignment of the medicament delivery device 1 relative to the needle assembly magazine 2 during attachment. For example, the aperture may be sized and shaped (e.g., cylindrical) to complement the distal end of the medicament delivery device 1. The coupling 9 may further include a distal aperture which is adapted to allow a needle to pass through to penetrate the septum 5 on the cartridge 4.

In an exemplary embodiment, a needle guard 10 is coupled to the housing 6 and capable of translating relative to the housing 6 between an extended position (shown in FIG. 2) and a retracted position. A guard spring 11 may bias the needle guard 10 in the extended position. The needle guard 10 and the housing 6 may be keyed to prevent relative rotation. The needle guard 10 includes a distal aperture 22 for allowing a needle to pass through.

In an exemplary embodiment, a needle assembly carrier 7 is rotatably coupled to a boss 12 on the needle guard 10. In an exemplary embodiment, the boss 12 is disposed on an axis which is in parallel with a longitudinal axis L of the medicament delivery device 1. The needle assembly carrier 7 is adapted to hold a plurality of needle assemblies 8. In an exemplary embodiment, the number of needle assemblies 8 may correspond to a number of doses of the medicament available in the cartridge 4. Clips 13 on the boss 12 may engage the needle assembly carrier 7 to prevent axial movement of the needle assembly carrier 7 relative to the boss 12.

In an exemplary embodiment, each needle assembly 8 comprises a double-tipped needle 8' and a needle hub 17 coupled to the needle 8'. The needle hub 17 is adapted to slidably fit within an aperture 18 formed in the needle assembly carrier 7. A distal end of the needle hub 17 includes clips 19 which are adapted to engage a distal face of the needle assembly carrier 7 to limit axial movement of the needle hub 17 relative to the needle assembly carrier 7 in a proximal direction P. A proximal end of the needle hub 17 includes a flange adapted to support a needle spring 20 grounded on a proximal face of the needle assembly carrier 7. The needle assembly 8 can move between an extended position and a retracted position (shown in FIG. 2), and the needle spring 20 biases the needle assembly 8 in the refracted position.

Figure 3:
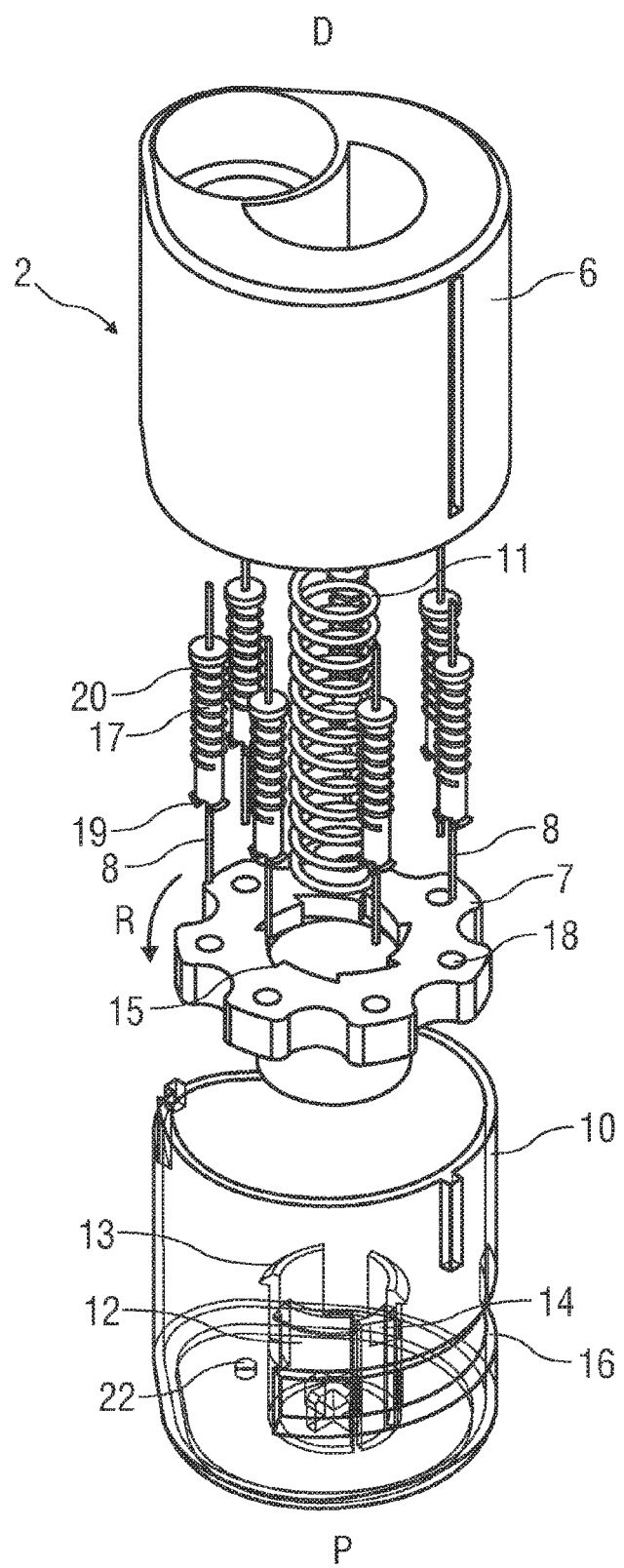
FIG. 3 is a schematic exploded view of an exemplary embodiment of a needle assembly magazine.

As shown in FIG. 3, a resilient radial arm 14 may be formed on the boss 12 and adapted to engage ratchets 15 on the needle assembly carrier 7. The radial arm 14 deflects when engaged by a ratchet 15 when the needle assembly carrier 7 rotates in a first rotational direction relative to the boss 12 but abuts the ratchet 15 and prevents rotation of the needle assembly carrier 7 in a second rotational direction relative to the boss 12 opposite the first rotational direction.

Further, a spacing between consecutive ratchets 15 may ensure that the needle assembly carrier 7 rotates a sufficient angular distance such that a needle assembly 8 is aligned with the medicament delivery device 1 and the distal aperture 22 on the needle guard 10.

In an exemplary embodiment, the needle assembly carrier 7 includes grip features, one or more of which may protrude, at any given time, through a cut-out 16 in the needle guard 10. The grip features may be pushed by a user, for example, to rotate the needle assembly carrier 7.

Figure 4:
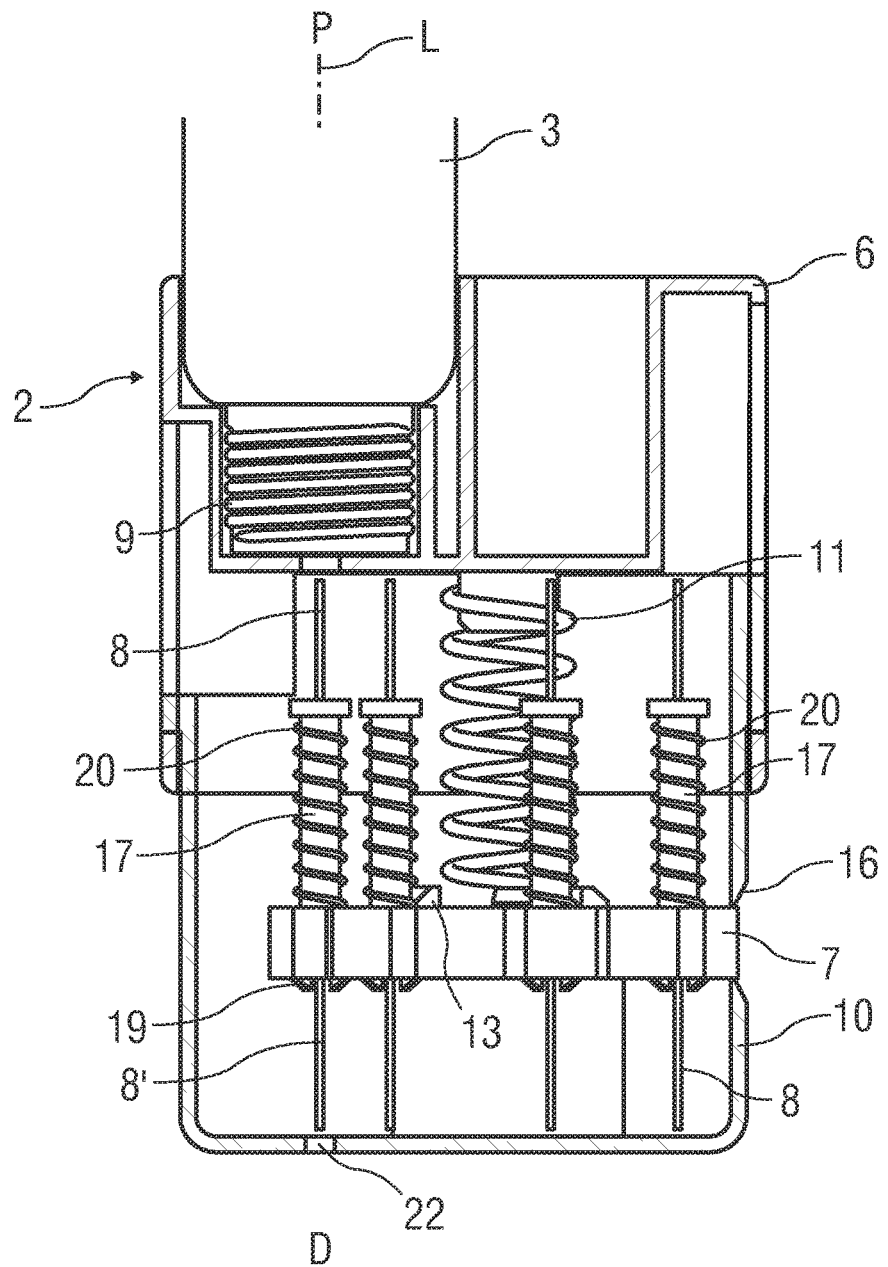
FIG. 4 is a schematic detail longitudinal section of an exemplary embodiment of a needle assembly magazine prior to use.

FIG. 4 shows an exemplary embodiment of a needle assembly magazine 2 according to the present invention prior to use. Prior to use, the needle guard 10 is in the extended position relative to the housing 6, and a needle assembly 8 has been aligned (e.g., by rotating the needle assembly carrier 7) with the distal apertures in the coupling 9 and the needle guard 10.

Figure 5:
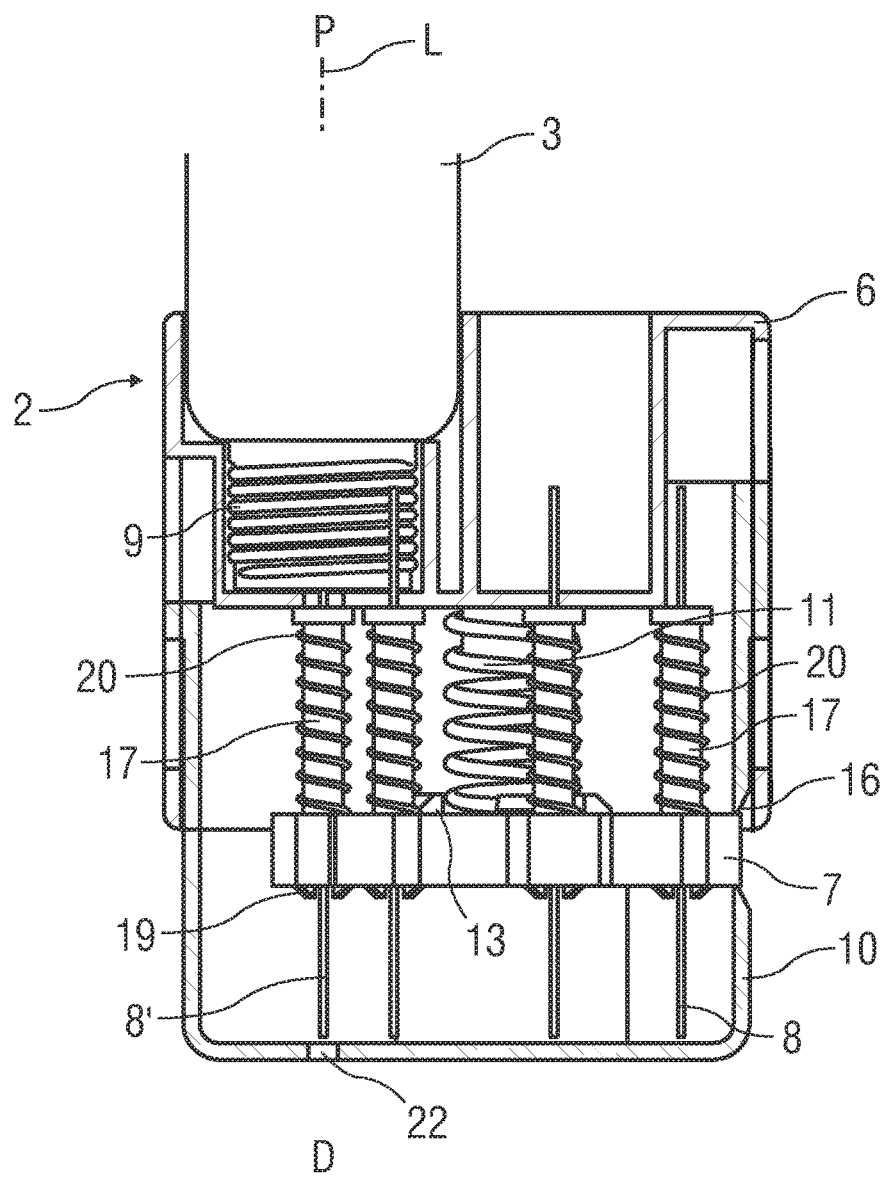
FIG. 5 is a schematic detail longitudinal section of an exemplary embodiment of a needle assembly magazine during use.

FIG. 5 shows an exemplary embodiment of a needle assembly magazine 2 according to the present invention during use. The medicament delivery device 1 is coupled to the needle assembly magazine 2. A distal face of the needle guard 10 is placed on an injection surface such that the distal aperture 22 overlies the injection site. A distally directed force is applied to the medicament delivery device 1 which causes the needle guard 10 to translate from the extended position toward the retracted position against the force of the guard spring 11, allowing the proximal tip of the needle 8' to pierce the septum 5 of the cartridge 4.

Figure 6:
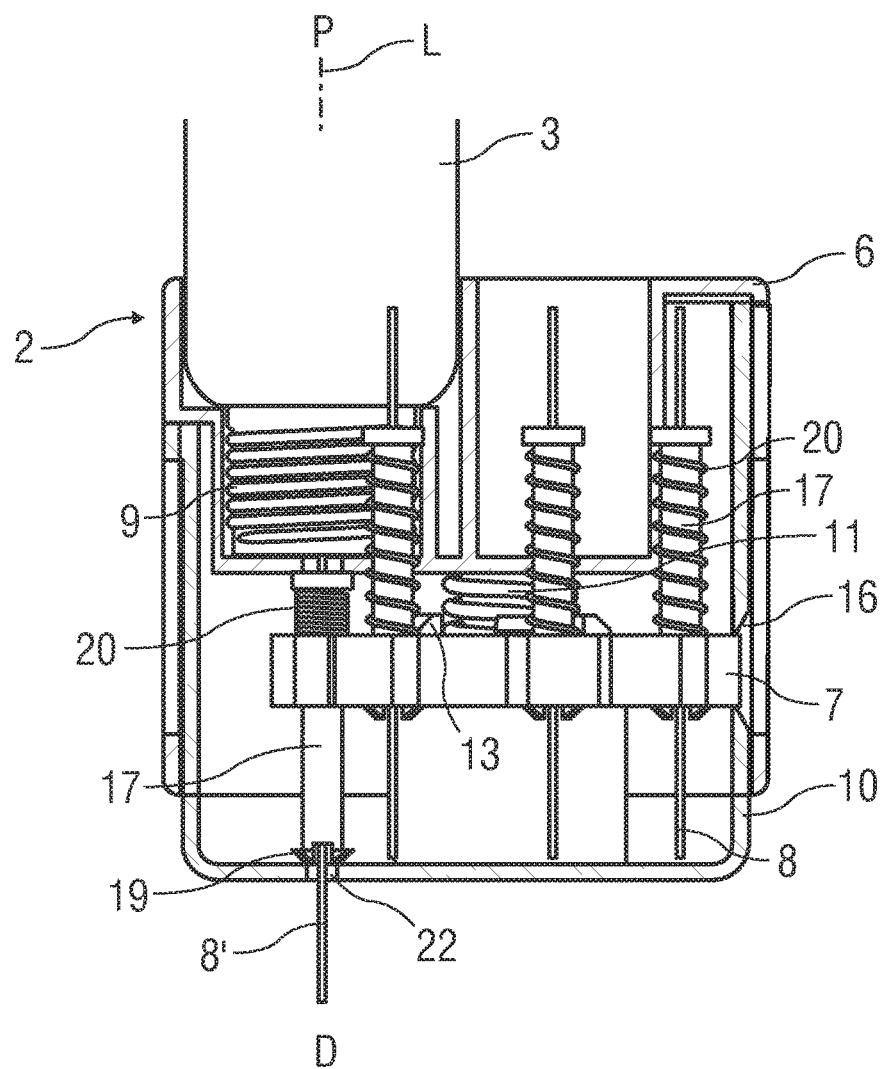
FIG. 6 is a schematic detail longitudinal section of an exemplary embodiment of a needle assembly magazine during use.

FIG. 6 shows an exemplary embodiment of a needle assembly magazine 2 according to the present invention during use. Further distally directed force applied to the medicament delivery device 1 causes the needle guard 10 to translate into the retracted position. The coupling 9 engages the proximal flange on the needle assembly hub 17 and pushing the needle hub 17 (and the needle 8') in the distal direction from the retracted position to the extended position against the biasing force of the needle spring 20, such that the distal tip of the needle 8' passes through the distal aperture 22 of the needle guard 10 and pierces the injection site.

Figure 7:
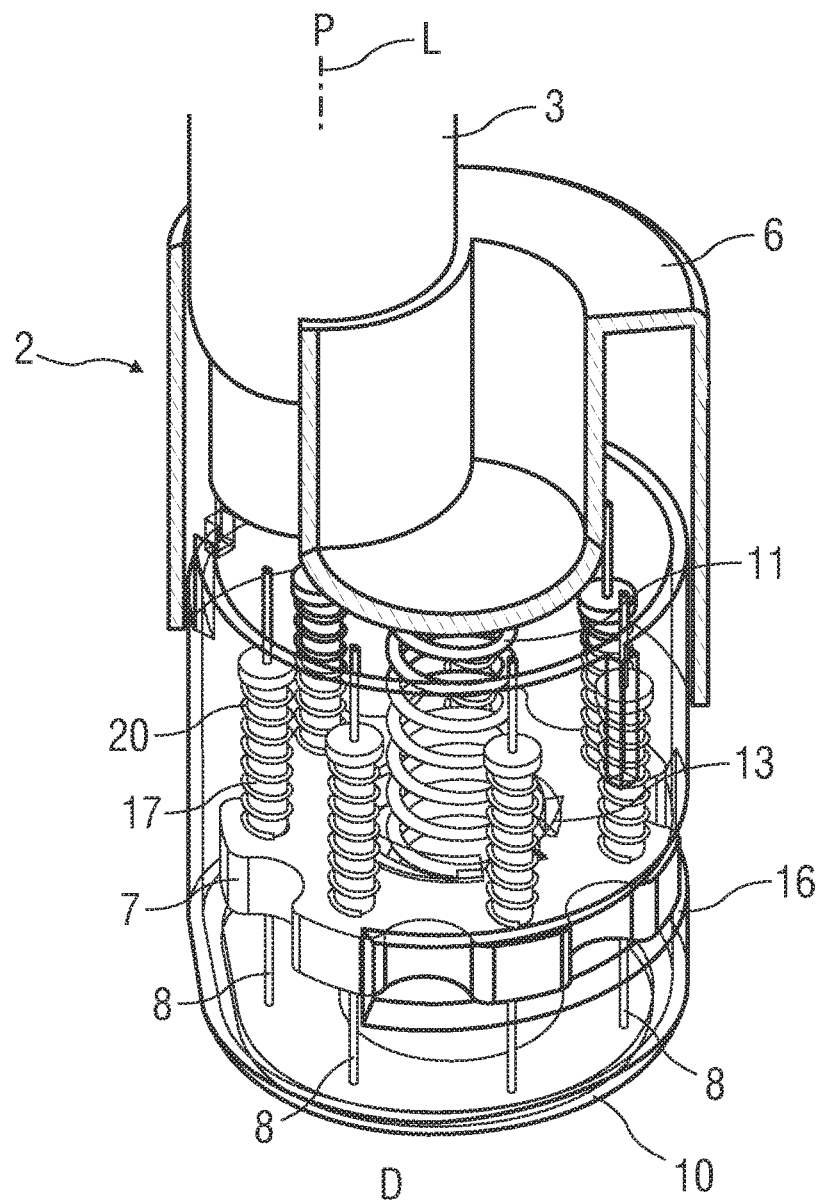
FIG. 7 is a schematic perspective view of an exemplary embodiment of a needle assembly magazine after use.

FIG. 7 shows an exemplary embodiment of a needle assembly magazine 2 according to the present invention after use. When the force on the medicament delivery device 1 is reduced or released, or when the needle assembly magazine 2 is removed from the injection site, the biasing force of the needle spring 20 causes the needle assembly 8 to translates from the extended position to the retracted position, and the biasing force of the guard spring 11 causes the needle guard 10 to translate from the retracted position to the extended position.

Figure 9:
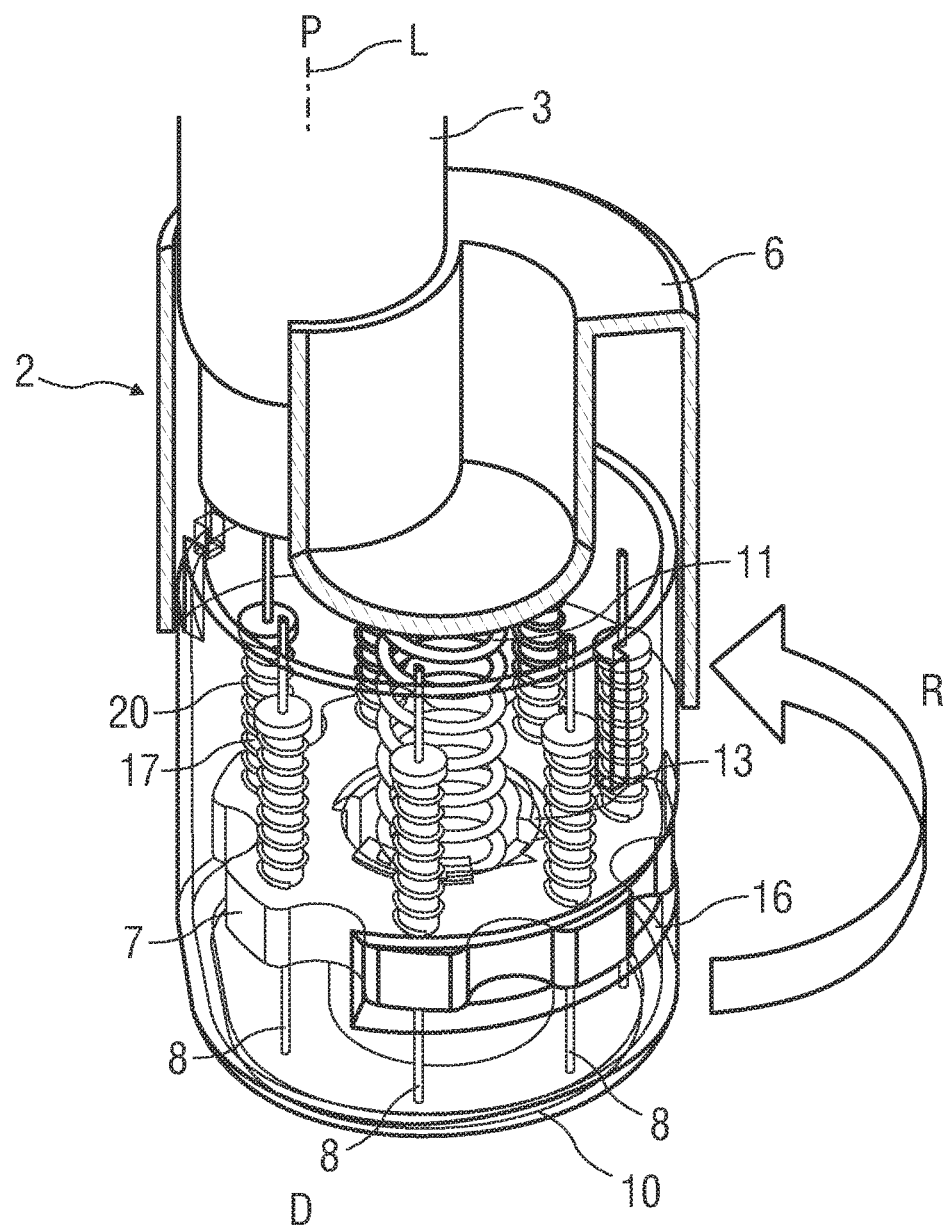
FIG. 9 is a schematic perspective view of an exemplary embodiment of a needle assembly magazine being prepared for subsequent use.

FIG. 9 shows an exemplary embodiment of a needle assembly magazine 2 according to the present invention being prepared for a subsequent injection. When a subsequent injection is required, the grip features may be used to rotate the needle assembly carrier 7 relative to the boss 12 to align a new needle assembly 8 with the distal apertures of the coupling 9 and the needle guard 10.

Figure 8:
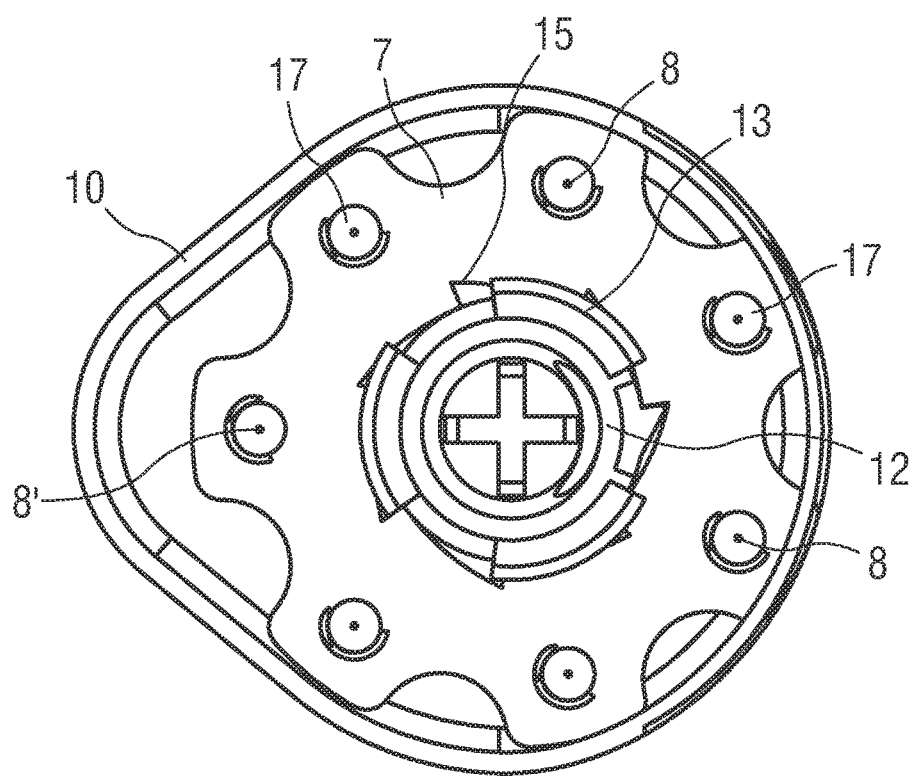
FIG. 8 is a schematic cross section of an exemplary embodiment of a needle assembly magazine being prepared for subsequent use.
Figure 10:
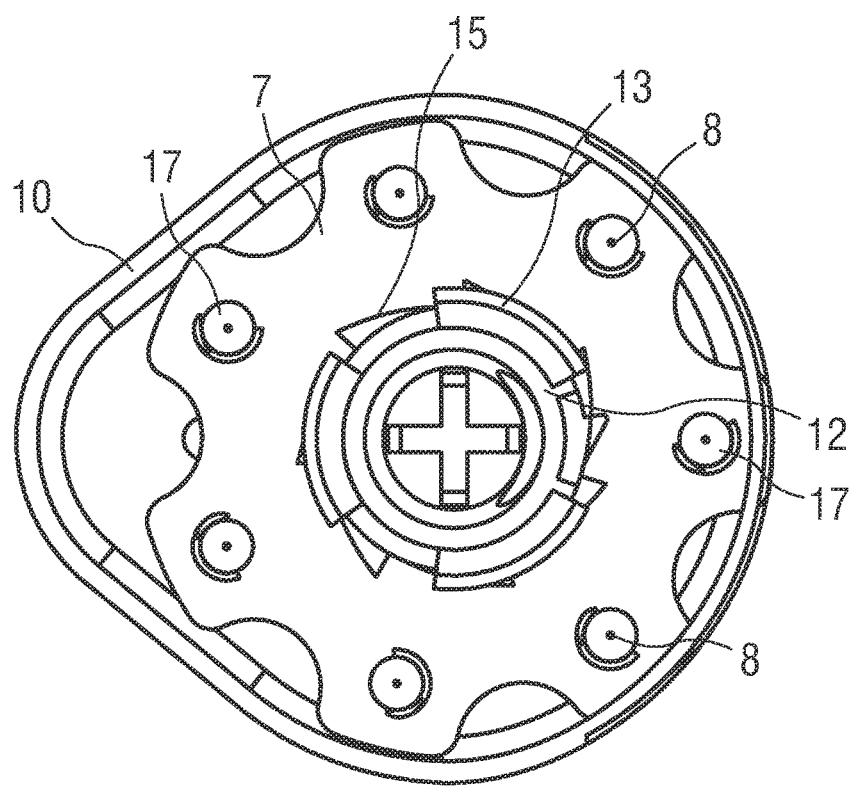
FIG. 10 is a schematic cross section of an exemplary embodiment of a needle assembly magazine being prepared for subsequent use.

FIGS. 8 and 10 show exemplary embodiments of a needle assembly magazine 2 according to the present invention being prepared for a subsequent injection. In these figures, the needle assembly carrier 7 is being rotated relative to the boss 12 to align a new needle assembly 8 with the distal apertures of the coupling 9 and the needle guard 10. Engagement of the ratchets 15 and the resilient radial arm 14 provide a tactile feedback to the user. For example, rotational resistance may increase as a ratchet 15 engages and deflects the radial arm 14. When the ratchet 15 bypasses the radial arm 14, the rotational resistance may decrease providing a tactile feedback that the new needle assembly 8 is in a proper position. The radial arm 14 may prevent "rewinding" of the needle assembly carrier 7 so that a used needle assembly 8 is not reused.

Figure 11:
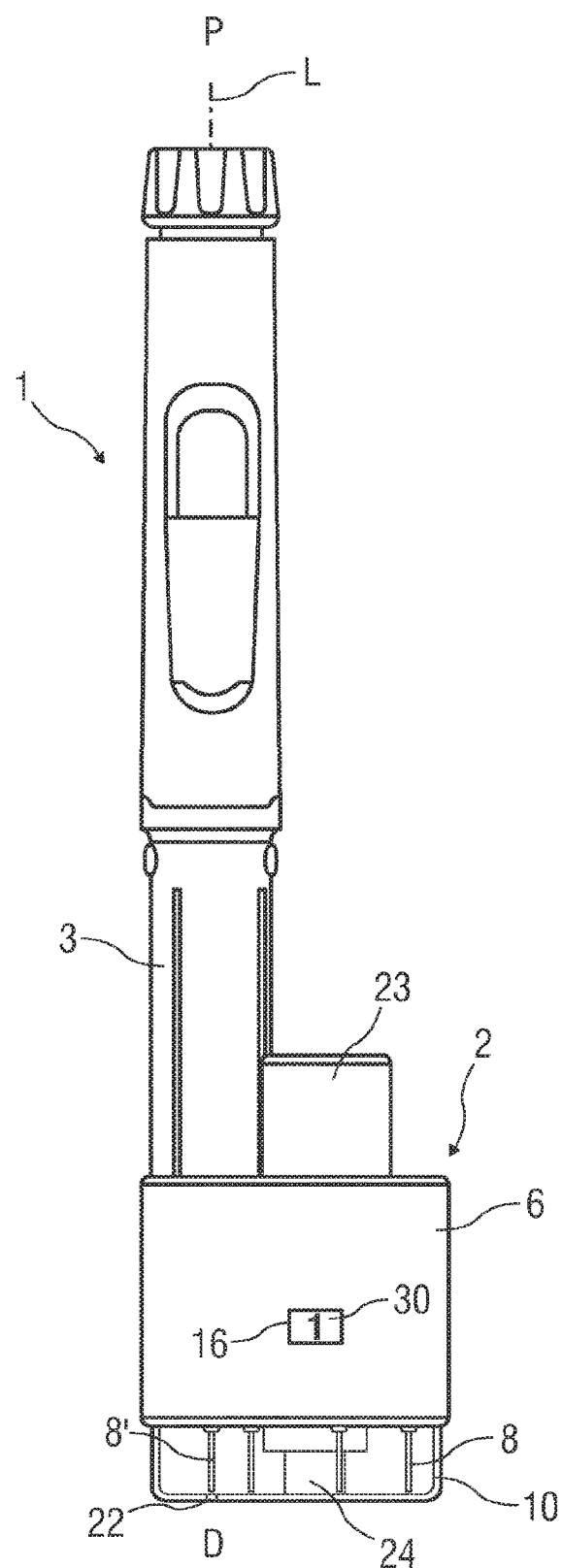
FIG. 11 is a schematic side view of another exemplary embodiment of a medicament delivery device with a needle assembly magazine.

FIG. 11 shows another exemplary embodiment of a needle assembly magazine according to the present invention. In this exemplary embodiment, the housing 6 includes a cut-out 16 for viewing an indicia (e.g., a number, a graphic, a symbol, a color) indicating a number of unused needle assemblies remaining, a number of used needle assemblies, etc. Thus, each time a needle assembly is used, the indicia may be updated to provide a visual feedback regarding use of the needle assembly magazine.

Figure 12:
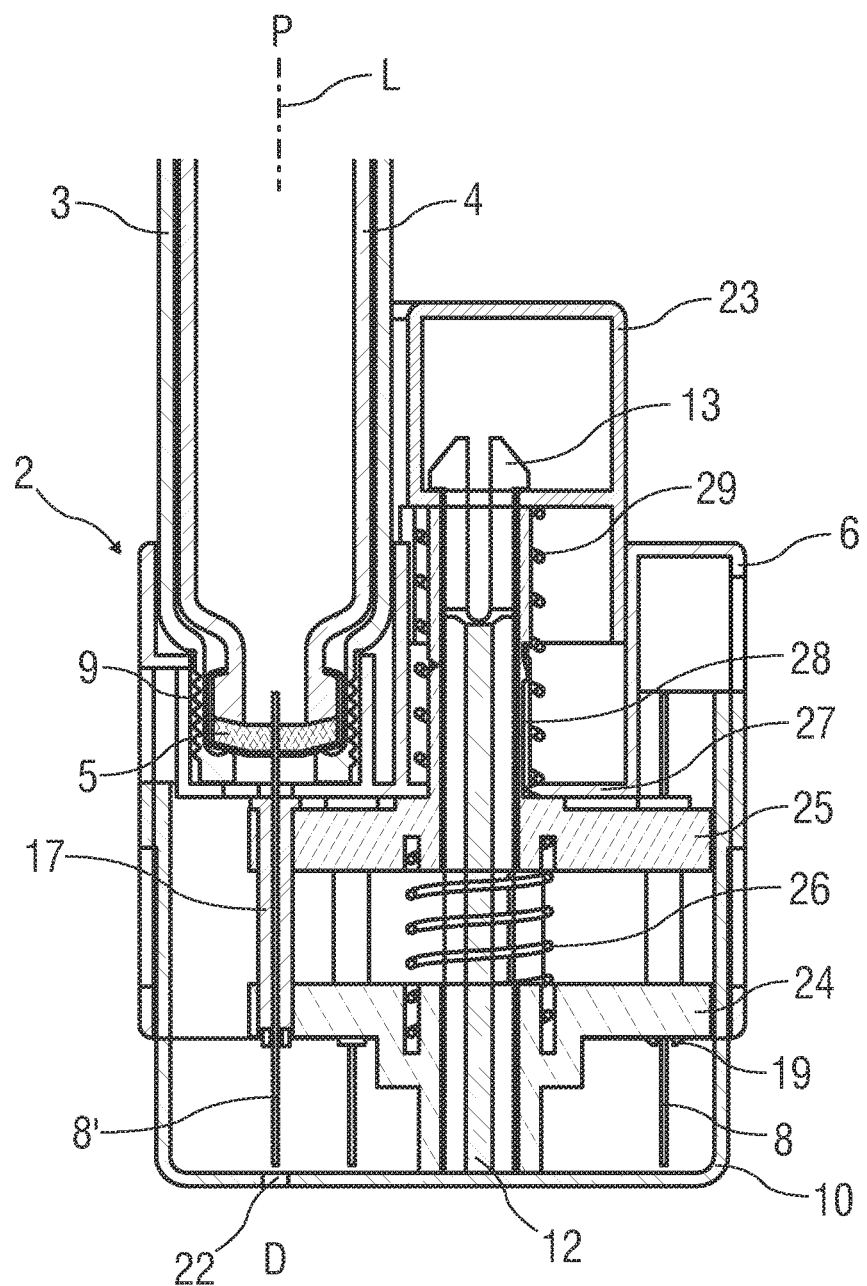
FIG. 12 is a schematic detail longitudinal section of another exemplary embodiment of a needle assembly magazine.

FIG. 12 shows another exemplary embodiment of a needle assembly magazine according to the present invention. In this exemplary embodiment, the needle assembly magazine 2 includes a needle assembly carrier 7 comprising a proximal plate 25 and a distal plate 24 which are both rotatably coupled to a boss 12. The proximal plate 25 is also slidably coupled to the boss 12. A carrier spring 26 biases the proximal plate 25 relative to the distal plate 24. The proximal plate 25 and the distal plate 24 include apertures for holding needle assemblies 8. In this exemplary embodiment, the needle assemblies 8 each include a needle hub 17 coupled to a needle 8' having a proximal tip and a distal tip.

In an exemplary embodiment, the needle assembly magazine 2 includes a button 23 slidably coupled to the housing 6. The button 23 includes an external surface adapted to be pressed by a user. Clips 13 on the boss 12 engage the button 23 for movement of the button 23 relative to the boss 12 beyond an extended position (shown in FIG. 12). A button spring 29 biases the button 23 toward the extended position. The button 23 is coupled to the proximal plate 25 so that pressing the button 23 into a retracted position displaces the proximal plate 25 relative to the boss 12.

Figure 13:
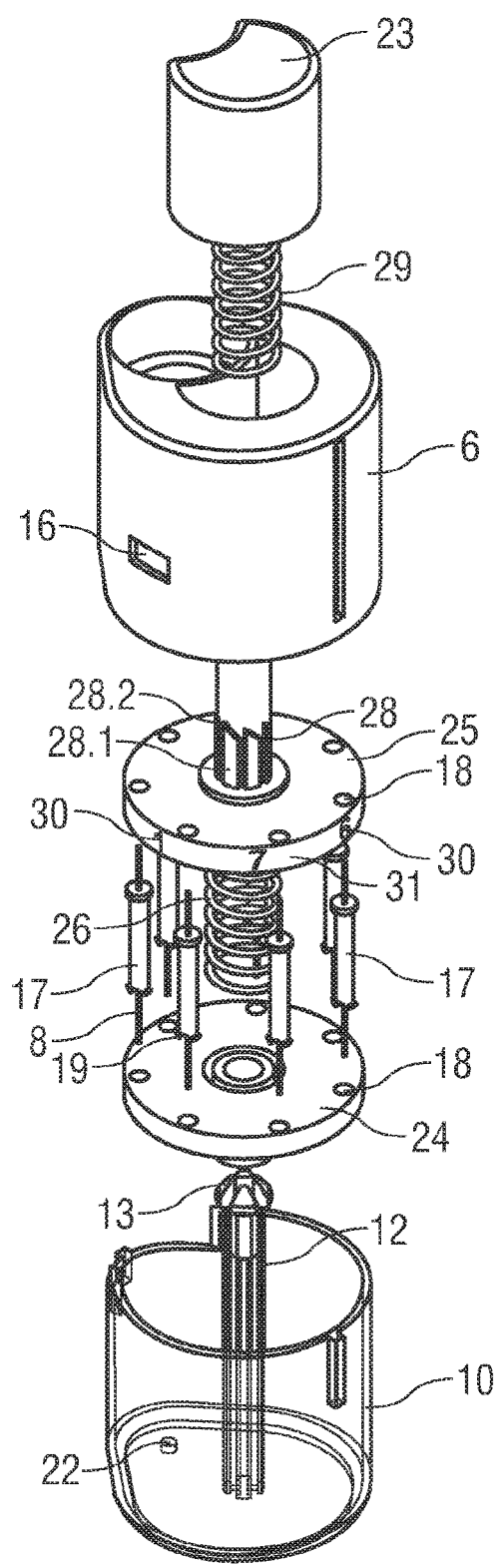
FIG. 13 is a schematic exploded view of another exemplary embodiment of a needle assembly magazine.

As shown in the exemplary embodiment in FIG. 13, the housing 6 includes a drive tooth 27 adapted to engage a track 28 coupled to the proximal plate 25. The track 28 may be formed on a stem which extends proximally of the proximal plate 25, and the drive tooth 27 may be disposed radially on the housing 6 to engage the track 28. In an exemplary embodiment, the track 28 comprises a number of longitudinal channels 28.1 adapted to receive the drive tooth 27. When the drive tooth 27 is in a longitudinal channel 28.1, rotation of the proximal plate 25 relative to the needle guard 10 is prevented. The track 28 further comprises a number of angled portions 28.2 which connect consecutive longitudinal channels 28.1. As explained further below, when the button 23 is pressed, the drive tooth 27 travels from a first longitudinal channel 28.1 over an angled portion 28.2 to a second longitudinal channel 28.1, and the angled portion 28.2 causes the proximal plate 25 to rotate relative to the needle guard 10. Because the needle assemblies 8 are disposed in the apertures of the proximal and distal plates 25, 24, rotation of the proximal plate 25 results in corresponding rotation of the distal plate 24. In an exemplary embodiment, a angular space between consecutive longitudinal channels 28.1 corresponds to an angular space between consecutive needle assemblies 8 in the plates 24, 25, such that one depression of the button 23 causes rotation of the plates 24, 25 to align a needle assembly 8 with the distal apertures in the coupling 9 and the needle guard 10.

Referring back to FIG. 12, the needle assembly magazine 2 is in a pre-use position. The medicament delivery device 1 is coupled to the housing 6, the needle guard 10 is in the extended position, and the button 23 is in the extended position. When the medicament device is coupled to the housing 6, the proximal tip of the needle 8' in the needle assembly 8 aligned with the distal aperture of the coupling 9 penetrates the septum 5 of the cartridge 4. The needle guard 10 is maintained in the extended position, because the carrier spring 26 biases the plates 24, 25 relative to each other, and the proximal plate 25 abuts the housing 6 while the distal plate 24 abuts the needle guard 10.

When the needle guard 10 is in the extended position, the distal tip of the needle 8' on the needle assembly 8 aligned with the distal aperture 22 is covered. In fact, the housing 6 and the needle guard 10 may be made from an opaque material so that the needle 8' is never visible before, during or after use. In another exemplary embodiment, all or a portion of the housing 6 and/or the needle guard 10 may be translucent to allow visualization of the needle 8' and/or any other internal component of the needle assembly magazine 2.

Figure 14:
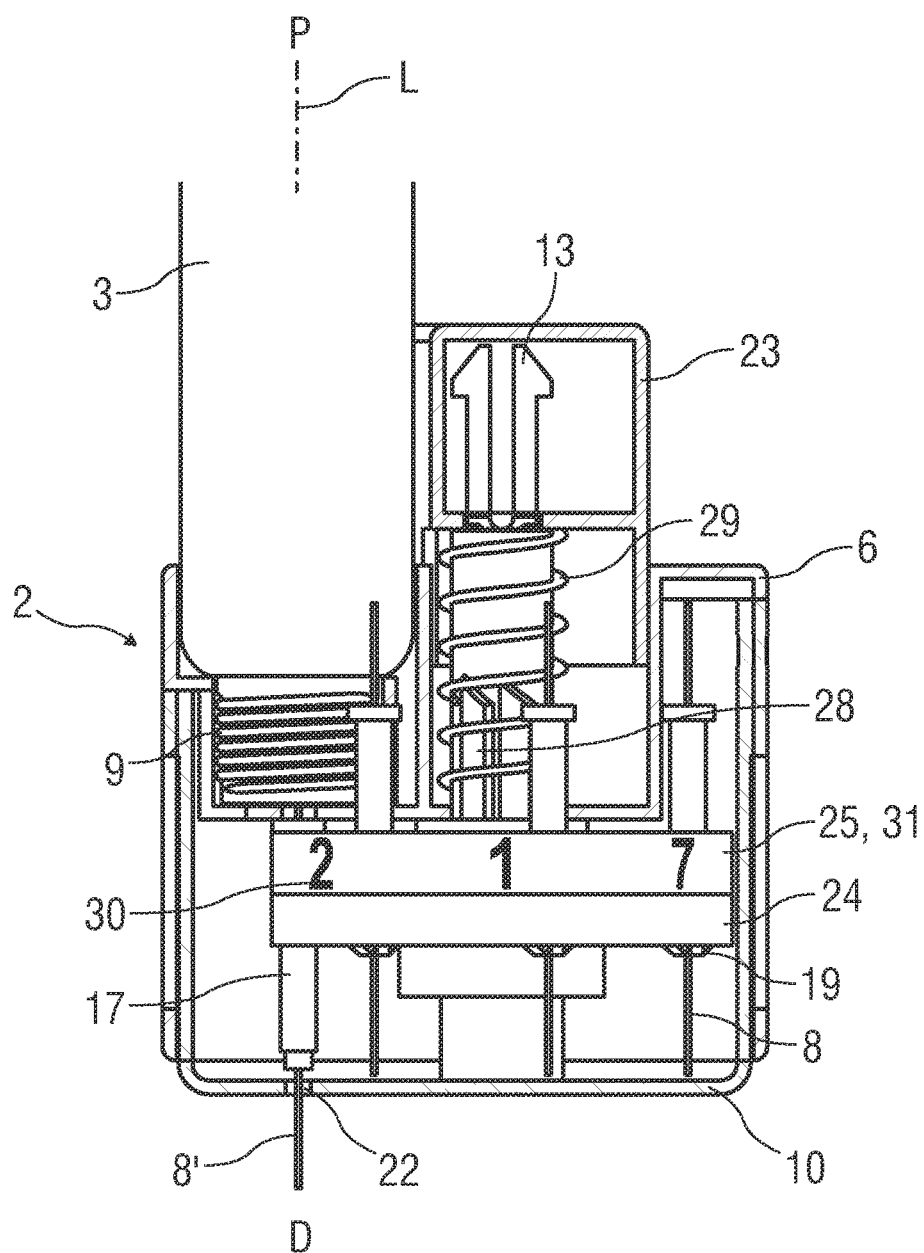
FIG. 14 is a schematic detail longitudinal section of another exemplary embodiment of a needle assembly magazine prior to use.

FIG. 14 shows an exemplary embodiment of a needle assembly magazine 2 during use. When the needle guard 10 is placed on an injection surface, the distal aperture 22 is aligned with the injection site. A distally directed force is applied to the medicament delivery device 1 which causes the needle guard 10 to translate from the extended position toward the retracted position against the force of the carrier spring 26, causing the distal plate 24 to move axially toward the proximal plate 25. The coupling 9 engages the proximal flange on the needle assembly hub 17 and pushing the needle hub 17 (and the needle 8) in the distal direction from the retracted position to the extended position, such that the distal tip of the needle 8' passes through the distal aperture 22 of the needle guard 10 and pierces the injection site.

When the force on the medicament delivery device 1 is reduced or released, or when the needle assembly magazine 2 is removed from the injection site, the biasing force of the carrier spring 26 causes the needle distal plate 24 to translate in the distal direction, which causes the needle guard 10 to translate from the retracted position to the extended position. In the extended position, the needle guard 10 covers the distal tip of the needle 8'.

Figure 15:
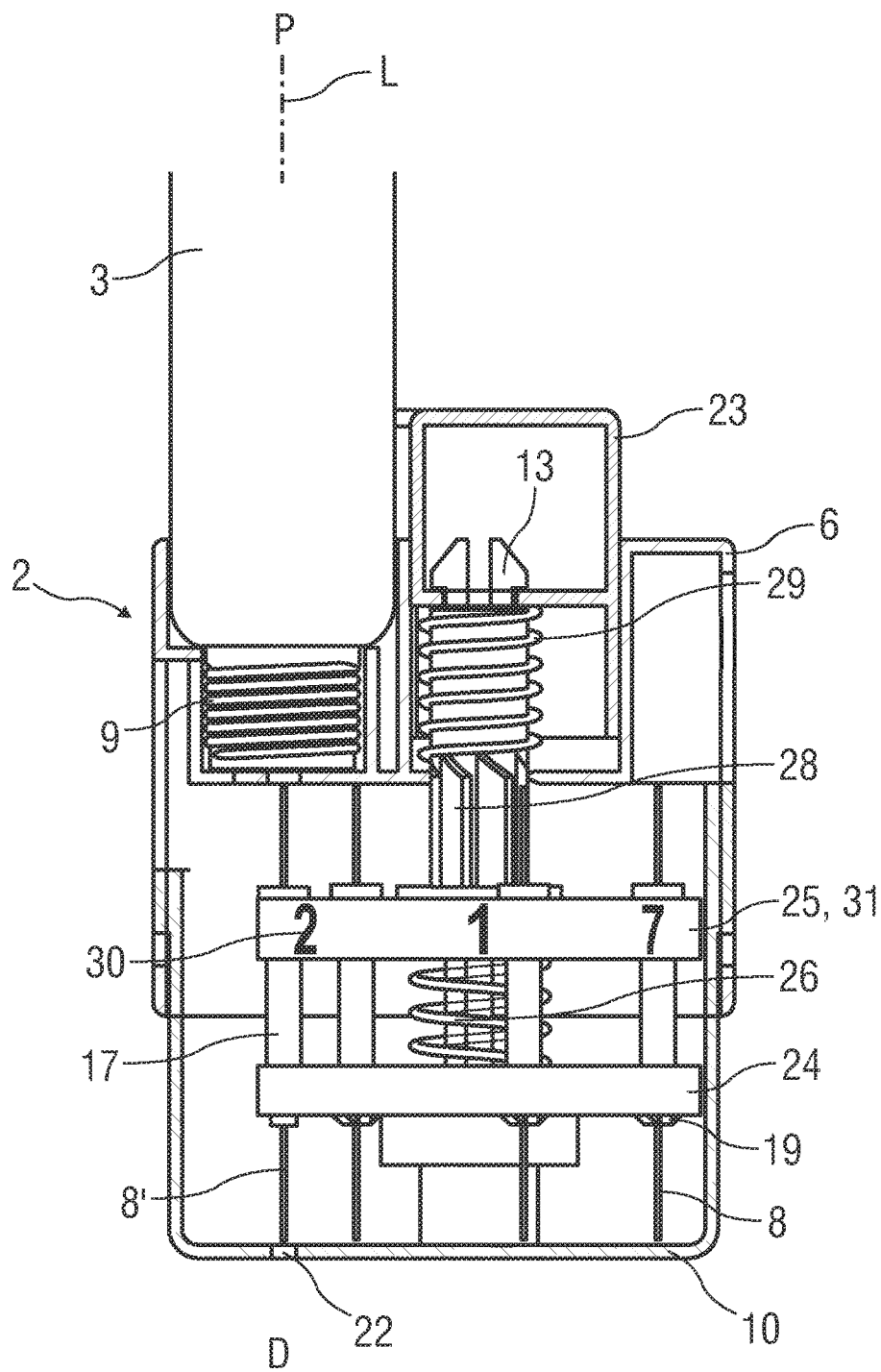
FIG. 15 is a schematic detail longitudinal section of another exemplary embodiment of a needle assembly magazine being prepared for subsequent use.

FIG. 15 shows an exemplary embodiment of a needle assembly magazine 2 according to the present invention being prepared for a subsequent injection. When a subsequent injection is required, the button 23 is pressed to displace the proximal plate 25. As the proximal plate 25 moves, it pushes the distal plate 24 in the distal direction via the carrier spring 26. This distal movement pulls the proximal tip of the needle 8' out of the cartridge 4 and the septum 5.

Figure 16:
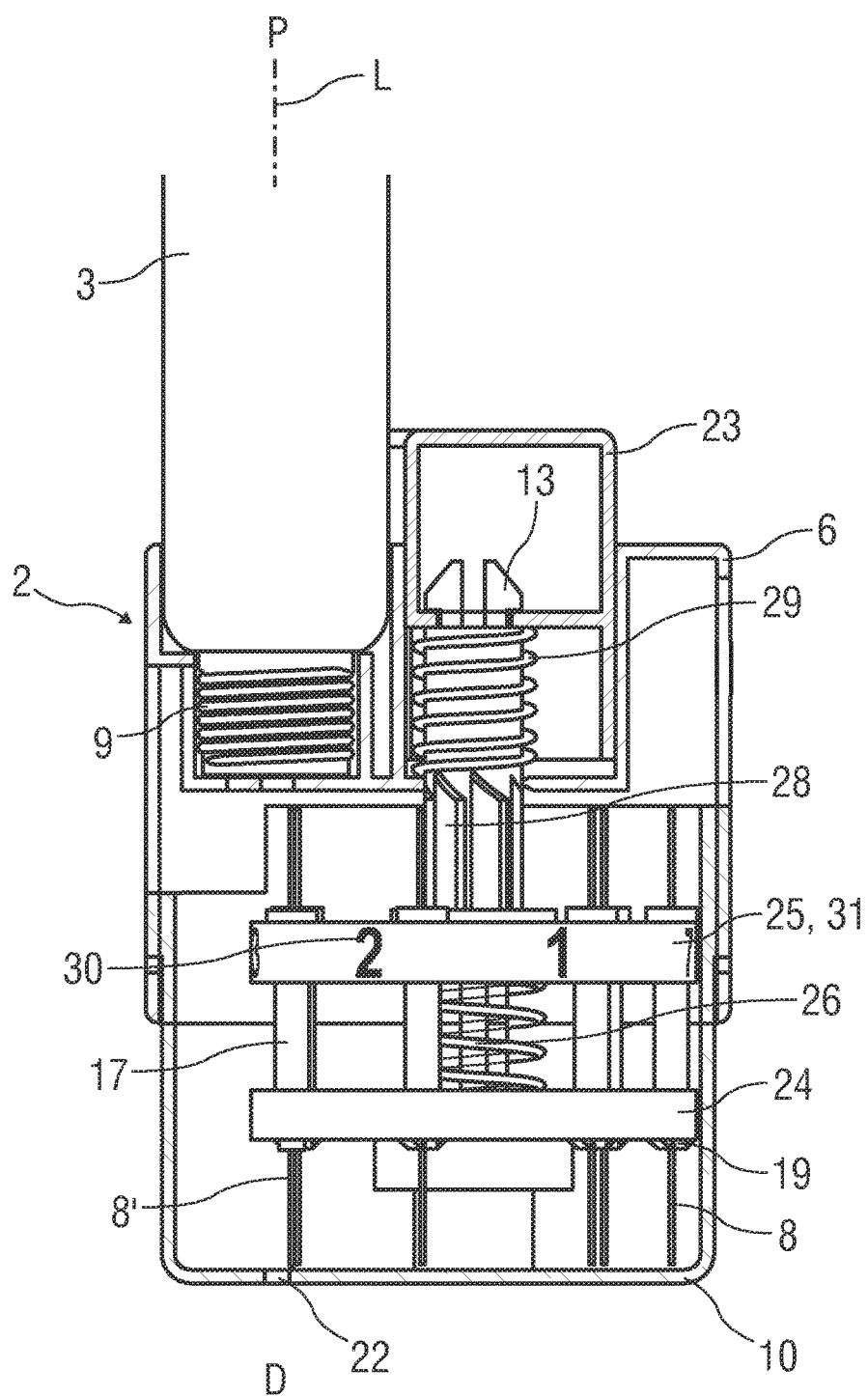
FIG. 16 is a schematic detail longitudinal section of another exemplary embodiment of a needle assembly magazine being prepared for subsequent use.

FIG. 16 shows an exemplary embodiment of a needle assembly magazine 2 according to the present invention being prepared for a subsequent injection. As the button 23 is pressed, the drive tooth 27 travels proximally within a first longitudinal channel 28.1. When the drive tooth 27 reaches the angled portion 28.2, the proximal plate 25, and thus the needle assemblies 8 and the distal plate 24, rotate relative to the housing 6 and the needle guard 10.

Figure 17:
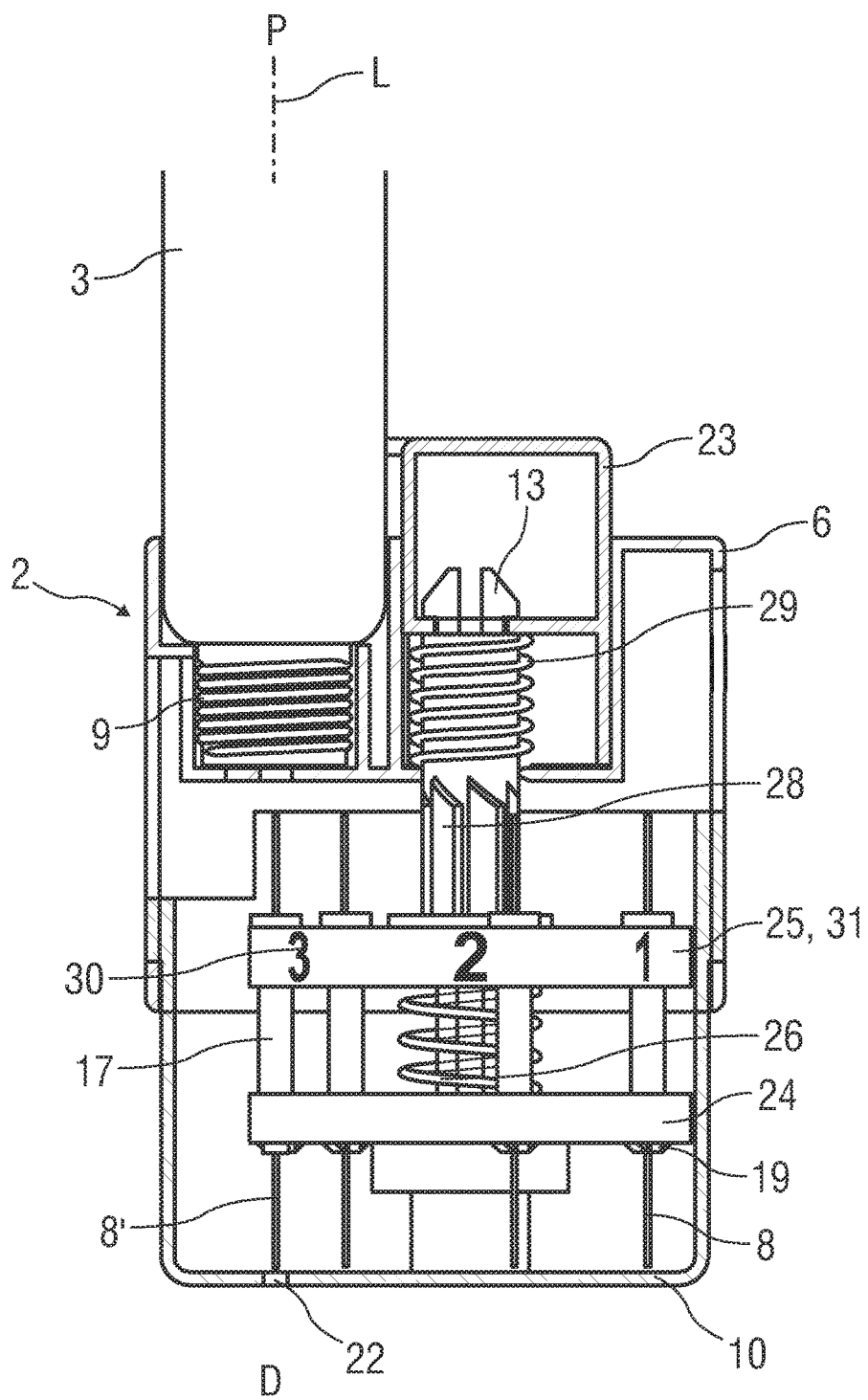
FIG. 17 is a schematic detail longitudinal section of another exemplary embodiment of a needle assembly magazine being prepared for subsequent use.

FIG. 17 shows an exemplary embodiment of a needle assembly magazine 2 according to the present invention being prepared for a subsequent injection. As the button 23 is fully pressed, the drive tooth 27 has entered or aligned with a second longitudinal channel 28.1, and the plates 24, 25 have rotated a sufficient angular distance such that a new needle assembly is aligned with the distal apertures in the coupling 9 and the needle guard 10.

Figure 18:
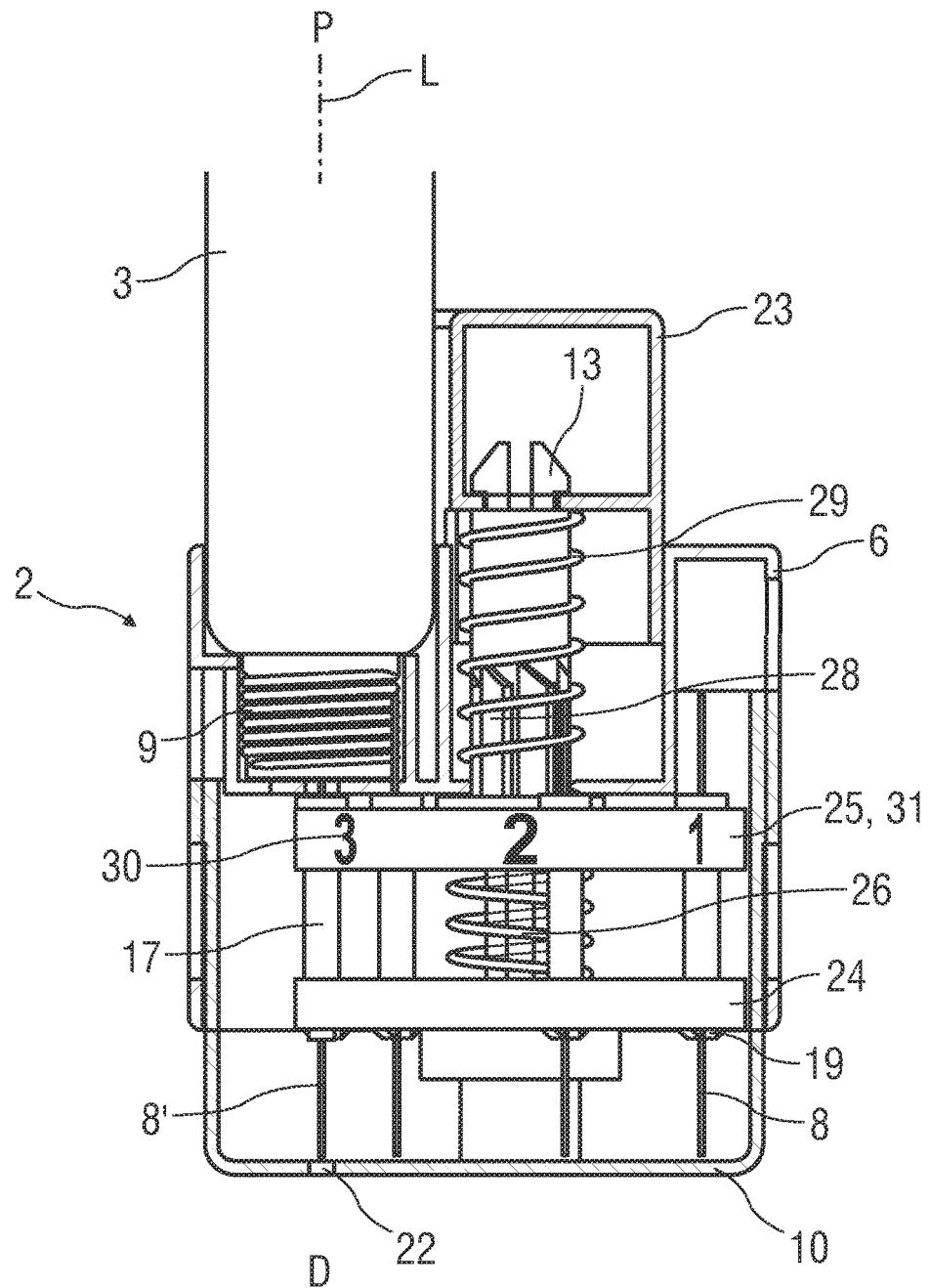
FIG. 18 is a schematic detail longitudinal section of another exemplary embodiment of a needle assembly magazine prepared for subsequent use.

FIG. 18 shows an exemplary embodiment of a needle assembly magazine 2 according to the present invention being prepared for a subsequent injection. When the button 23 is released, the plates 24, 25 and the needle guard 10 initial axial positions, and the proximal tip of the new needle 8' pierces the septum 5 of the cartridge 4. The drive tooth 27 travels down the second longitudinal portion 28.1 preventing further rotation of the plates 24, 25.

When the plates 24, 25 have finished rotating, a new indicia 30 is visible to provide a visual feedback about, for example, the number of unused needle assemblies 8 remaining, the number of needle assemblies 8 which have been used, whether all of the needle assemblies have been used, etc.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle assembly magazine comprising:
   a housing comprising a coupling having a proximal aperture adapted to receive a medicament delivery device and a distal aperture adapted to receive a needle of one of a plurality of needle assemblies, each of the plurality of needle assemblies comprising a needle hub adapted to hold the needle;
   a needle guard axially translatable relative to the housing from an extended position to a retracted position, the needle guard coupled to the housing, having a distal aperture axially aligned with the distal aperture of the coupling; and
   a needle assembly carrier rotatably coupled to the needle guard and adapted to hold the plurality of needle assemblies, the needle hub being slidably disposed in an aperture in the needle assembly carrier such that each of the needle assemblies is movable between a retracted position and an extended position relative to the needle assembly carrier,
   wherein the needle assembly carrier is rotatable to align a first needle assembly of the needle assemblies with the distal aperture of the coupling and the distal aperture of the needle guard,
   wherein, when the first needle assembly is aligned with the distal aperture of the coupling and the distal aperture of the needle guard, a movement of the needle guard from the extended position to the retracted position causes a movement of the needle hub of the first needle assembly from a retracted position of the needle hub of the first needle assembly to an extended position of the needle hub of the first needle assembly, and
   wherein the movement of the needle hub to the extended position of the needle hub of the first needle assembly causes the needle hub of the first needle assembly to abut the housing such that a proximal tip of the needle of the first needle assembly projects through the distal aperture of the coupling and into the coupling and a distal tip of the needle projects through the distal aperture of the needle guard.

2. The needle assembly magazine of claim 1, wherein the coupling comprises at least one of a thread, a bayonet arrangement, a friction fit arrangement, and a snap fit arrangement, and the coupling is adapted to engage a distal end of the medicament delivery device when the medicament delivery device is disposed in the housing.

3. The needle assembly magazine of claim 1, further comprising a guard spring biasing the needle guard toward the extended position of the needle guard.

4. The needle assembly magazine of claim 1, wherein the at least one of the needle assemblies further comprises a needle spring biasing at least one of the needle assemblies toward the retracted position of the needle assemblies.

5. The needle assembly magazine of claim 1, wherein: the needle assembly carrier comprises a plurality of ratchets adapted to engage a resilient arm on the needle guard, the resilient arm being configured such that, when the needle assembly carrier rotates in a first rotational direction about a longitudinal axis of the needle assembly magazine, the resilient arm engages with one of the plurality of ratchets, deflects due to engagement with the one of the plurality of ratchets, and abuts the one of the plurality of ratchets to prevent rotation of the needle assembly carrier in a second rotational direction about the longitudinal axis of the needle assembly magazine.

6. The needle assembly magazine of claim 1, wherein the needle assembly carrier comprises a plurality of grip features, wherein at least one of the plurality of grip features extends through a cut-out in the needle guard.

7. The needle assembly magazine of claim 1, wherein an indicia is disposed on the needle assembly carrier and is viewable through a cut-out in the needle guard.

8. The needle assembly magazine of claim 7, wherein the indicia comprises at least one of a number, a graphic, an image, a word, and a color and is indicative of at least one of a quantity of unused needle assemblies held in the needle assembly carrier and a quantity of used needle assemblies held in the needle assembly carrier.

9. The needle assembly magazine of claim 1, wherein the needle assembly carrier comprises a proximal plate and a distal plate, the proximal plate and the distal plate each comprising an aperture for holding one of each of the plurality of needle assemblies.

10. The needle assembly magazine of claim 9, further comprising:
a carrier spring biasing the proximal plate away from the distal plate.

11. The needle assembly magazine of claim 9, wherein the proximal plate comprises a stem having a track adapted to engage a drive tooth on the housing.

12. The needle assembly magazine of claim 11, wherein the track comprises a first longitudinal channel and a second longitudinal channel coupled by an angled portion.

13. The needle assembly magazine of claim 12, further comprising:
a button coupled to the housing and adapted to engage the proximal plate.

14. The needle assembly magazine of claim 13, wherein the button is axially movable relative to the housing between an extended position of the button and a retracted position of the button such that an axial movement of the button to the retracted position of the button causes the drive tooth to travel axially in the first longitudinal channel and an axial movement of the button to the extended position of the button causes the drive tooth to travel along the angled portion into the second longitudinal channel and the proximal plate to rotate relative to the needle guard.

15. The needle assembly magazine of claim 14, further comprising:
a button spring biasing the button toward the extended position of the button.

16. An auto-injector system comprising:
an auto-injector; and
a needle assembly magazine engaged to a distal end of the auto-injector, the needle assembly magazine comprising:
a housing comprising a coupling having a proximal aperture and a distal aperture, the proximal aperture of the coupling being engaged to the distal end of the auto-injector, the distal aperture of the coupling being adapted to receive a needle of one of a plurality of needle assemblies, each of the plurality of needle assemblies comprising a needle hub adapted to hold the needle;
a needle guard axially translatable relative to the housing from an extended position to a retracted position, the needle guard coupled to the housing, having a distal aperture axially aligned with the distal aperture of the coupling, and
a needle assembly carrier rotatably coupled to the needle guard and adapted to hold the plurality of needle assemblies, the needle hub being slidably disposed in an aperture in the needle assembly carrier such that each of the needle assemblies is movable between a retracted position and an extended position relative to the needle assembly carrier,
the needle assembly carrier being rotatable to align a first needle assembly of the plurality of needle assemblies with the distal aperture of the coupling and the distal aperture of the needle guard, wherein, when the first needle assembly is aligned with the distal aperture of the coupling and the distal aperture of the needle guard, a movement of the needle guard from the extended position to the retracted position causes a movement of the needle hub of the first needle assembly from a retracted position of the needle hub of the first needle assembly to an extended position of the needle hub of the first needle assembly, and
wherein the movement of the needle hub to the extended position of the needle hub of the first needle assembly causes the needle hub of the first needle assembly to abut the housing such that a proximal tip of the needle of the first needle assembly projects through the distal aperture of the coupling and into the coupling and a distal tip of the needle projects through the distal aperture of the needle guard.

17. A method of using a medicament delivery device with a needle assembly magazine to deliver a medicament to a patient, the method comprising:
inserting the medicament delivery device into a proximal aperture of a housing of the needle assembly magazine to engage the medicament delivery device with the needle assembly magazine such that a cartridge of the medicament delivery device aligns with a first needle assembly of a plurality of needle assemblies held within a needle assembly carrier of the needle assembly magazine, the cartridge containing the medicament and the first needle assembly comprising a needle;
placing a distal face of a needle guard of the needle assembly magazine against an injection site of the patient and applying a force to the needle assembly magazine toward the injection site such that the needle guard and the needle carrier move from an extended position to a retracted position with respect to the housing such that the housing abuts a needle hub of the first needle assembly and projects a distal tip of the needle through a distal aperture of the guard and pierces the injection site and projects a proximal tip of the needle into the cartridge;

delivering medicament from a cartridge through the needle to the patient;

removing the needle guard from the injection site; and rotating the needle assembly carrier relative to the medicament delivery device to align a second needle assembly of the plurality of needle assemblies.

\* \* \* \* \*